(12) United States Patent
Addison et al.

(10) Patent No.: US 10,219,705 B2
(45) Date of Patent: *Mar. 5, 2019

(54) SYSTEM AND METHOD FOR IDENTIFYING AUTOREGULATION ZONES

(71) Applicant: COVIDIEN LP, Mansfield, MA (US)

(72) Inventors: Paul S. Addison, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 194 days.

This patent is subject to a terminal disclaimer.

(21) Appl. No.: 15/146,595

(22) Filed: May 4, 2016

(65) Prior Publication Data

US 2016/0324425 A1 Nov. 10, 2016

Related U.S. Application Data

(60) Provisional application No. 62/158,659, filed on May 8, 2015.

(51) Int. Cl.
| | | |
|---|---|---|
| *A61B 5/02* | (2006.01) | |
| *A61B 5/0205* | (2006.01) | |
| *A61B 5/1455* | (2006.01) | |
| *A61B 5/00* | (2006.01) | |
| *G16H 50/20* | (2018.01) | |

(Continued)

(52) U.S. Cl.
CPC ............ *A61B 5/0205* (2013.01); *A61B 5/021* (2013.01); *A61B 5/02028* (2013.01); *A61B 5/14551* (2013.01); *A61B 5/14553* (2013.01); *A61B 5/4064* (2013.01); *A61B 5/6801* (2013.01); *A61B 5/7264* (2013.01);

(Continued)

(58) Field of Classification Search
CPC .............. A61B 5/0205; A61B 5/02028; A61B 5/14551

See application file for complete search history.

(56) References Cited

U.S. PATENT DOCUMENTS

| 4,776,339 A | 10/1988 | Schreiber |
|---|---|---|
| 5,351,685 A | 10/1994 | Potratz |

(Continued)

FOREIGN PATENT DOCUMENTS

| EP | 615723 A1 | 9/1994 |
|---|---|---|
| WO | WO9843071 A1 | 10/1998 |

(Continued)

OTHER PUBLICATIONS

International Search Report and Written Opinion for PCT Application No. PCT/US2016/031021 dated Aug. 5, 2016; 12 pgs.

(Continued)

*Primary Examiner* — Eric D. Bertram
(74) *Attorney, Agent, or Firm* — Shumaker & Sieffert, P.A.

(57) ABSTRACT

A method for monitoring autoregulation includes using a processor for receiving one or more physiological signals, determining a correlation-based measure indicative of the patient's autoregulation based on the one or more physiological signals, calculating a data clustering metric indicative of a distribution of the correlation-based measure within a window of blood pressures, and determining whether the window of blood pressures is within an intact autoregulation zone or an impaired autoregulation zone based at least in part on the data clustering metric.

21 Claims, 5 Drawing Sheets

(51) Int. Cl.
  *A61B 5/021* (2006.01)
  *G06F 19/00* (2018.01)
(52) U.S. Cl.
  CPC .......... *A61B 5/7275* (2013.01); *G06F 19/00* (2013.01); *G16H 50/20* (2018.01)

(56) References Cited

U.S. PATENT DOCUMENTS

| | | | |
|---|---|---|---|
| 5,482,034 | A | 1/1996 | Lewis et al. |
| 5,533,507 | A | 7/1996 | Potratz |
| 5,577,500 | A | 11/1996 | Potratz |
| 5,584,296 | A | 12/1996 | Cui et al. |
| 5,626,140 | A | 5/1997 | Feldman et al. |
| 5,803,910 | A | 9/1998 | Potratz |
| 5,934,277 | A | 8/1999 | Mortz |
| 6,385,471 | B1 | 5/2002 | Mortz |
| 6,438,399 | B1 | 8/2002 | Kurth |
| 6,453,183 | B1 | 9/2002 | Walker |
| 6,505,060 | B1 | 1/2003 | Norris |
| 6,510,329 | B2 | 1/2003 | Heckel |
| 6,599,251 | B2 | 7/2003 | Chen et al. |
| 6,668,182 | B2 | 12/2003 | Hubelbank |
| 6,714,803 | B1 | 3/2004 | Mortz |
| 6,754,516 | B2 | 6/2004 | Mannheimer |
| 6,896,661 | B2 | 5/2005 | Dekker |
| 6,987,994 | B1 | 1/2006 | Mortz |
| 7,001,337 | B2 | 2/2006 | Dekker |
| 7,221,969 | B2 | 5/2007 | Stoddart et al. |
| 7,268,873 | B2 | 9/2007 | Sevick-Muraca et al. |
| 7,744,541 | B2 | 6/2010 | Baruch et al. |
| 8,556,811 | B2 | 10/2013 | Brady |
| 2004/0097797 | A1 | 5/2004 | Porges et al. |
| 2005/0004479 | A1 | 1/2005 | Townsend et al. |
| 2005/0033129 | A1 | 2/2005 | Edgar, Jr. et al. |
| 2005/0192488 | A1 | 9/2005 | Bryenton et al. |
| 2005/0192493 | A1 | 9/2005 | Wuori |
| 2007/0004977 | A1 | 1/2007 | Norris |
| 2007/0049812 | A1 | 3/2007 | Aoyagi et al. |
| 2008/0081974 | A1 | 4/2008 | Pay |
| 2008/0146901 | A1 | 6/2008 | Katura et al. |
| 2008/0200785 | A1 | 8/2008 | Fortin |
| 2008/0228053 | A1 | 9/2008 | Wang et al. |
| 2009/0326386 | A1 | 12/2009 | Sethi et al. |
| 2010/0010322 | A1 | 1/2010 | Brady |
| 2010/0030054 | A1* | 2/2010 | Baruch ............... A61B 5/02007 600/368 |
| 2010/0049082 | A1 | 2/2010 | Hu et al. |
| 2011/0046459 | A1 | 2/2011 | Zhang et al. |
| 2011/0105912 | A1* | 5/2011 | Widman ............ A61B 5/02028 600/483 |
| 2012/0149994 | A1 | 6/2012 | Luczyk et al. |
| 2012/0253211 | A1* | 10/2012 | Brady ................ A61B 5/02028 600/507 |
| 2012/0271130 | A1 | 10/2012 | Benni |
| 2013/0190632 | A1* | 7/2013 | Baruch ................ A61B 5/4064 600/484 |
| 2014/0073888 | A1* | 3/2014 | Sethi ...................... A61B 5/021 600/324 |
| 2014/0275818 | A1 | 9/2014 | Kassem et al. |
| 2014/0278285 | A1 | 9/2014 | Marmarelis et al. |
| 2016/0106372 | A1* | 4/2016 | Addison ............. A61B 5/7221 600/324 |
| 2016/0345913 | A1 | 12/2016 | Montgomery et al. |
| 2016/0367197 | A1 | 12/2016 | Addison et al. |
| 2017/0000395 | A1 | 1/2017 | Addison et al. |
| 2017/0000423 | A1 | 1/2017 | Addison et al. |
| 2017/0095161 | A1 | 4/2017 | Addison et al. |
| 2017/0105631 | A1 | 4/2017 | Addison et al. |
| 2017/0105672 | A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | WO2016182853 A1 | 11/2016 |

OTHER PUBLICATIONS

Addison, P. S., et al.; "Low-Oscillation Complex Wavelets," Journal of Sound and Vibration, 2002, vol. 254, Elsevier Science Ltd., pp. 1-30.

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

(56) References Cited

OTHER PUBLICATIONS

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Cysewska-Sobusaik, Anna; "Metrological Problems With noninvasive Transillumination of Living Tissues," *Proceedings of SPIE*, vol. 4515, pp. 15-24 (2001).
Czosnyka, Marek, et al.; "Monitoring of cerebrovascular autoregulation: Facts, Myths, and Missing Links," Neurocrit Care (2009) 10:373-386.
Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.
Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.
Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.
East, Christine E., et al.; "Fetal Oxygen Saturation and Uterine Contractions During Labor," *American Journal of Perinatology*, vol. 15, No. 6, pp. 345-349 (Jun. 1998).
Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.
Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.
Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
Ge, Z.; "Significance tests for the wavelet cross spectrum and wavelet linear coherence," Annales Geophysicae, 2008, 26, Copernicus Publications on behalf of European Geosciences Union, pp. 3819-3829.
Gesquiere, Michael J., et al., "Impact of withdrawal of 450 ML of blook on respiration-induced oscillations of the ear plethysmographic waveform," Journal of Clinical Monitoring and Computing (2007) 21:277-282.
Goldman, Julian M.; "Masimo Signal Extraction Pulse Oximetry," *Journal of Clinical Monitoring and Computing*, vol. 16, pp. 475-483 (2000).
Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.
Hamilton, Patrick S., et al.; "Effect of Adaptive Motion-Artifact Reduction on QRS Detection," *Biomedical Instrumentation & Technology*, pp. 197-202 (May-Jun. 2000).
Huang, J., et al.; "Low Power Motion Tolerant Pulse Oximetry," Anesthesia & Analgesia 2002 94: S103.
Johansson, A.; "Neural network for photoplethysmographic respiratory rate monitoring," Medical & Biological Engineering & Computing, vol. 41, pp. 242-248 (2003).
Kaestle, S.; "Determining Artefact Sensitivity of New Pulse Oximeters in Laboratory Using Signals Obtained from Patient," *Biomedizinische Technik*, vol. 45 (2000).
Kim, J.M., et al.; "Signal Processing Using Fourier & Wavelet Transform for pulse oximetry," pp. II-310-II-311 (2001).
Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).
Leahy, Martin J., et al.; "Sensor Validation in Biomedical Applications," *IFAC Modelling and Control in Biomedical Systems*, Warwick, UK; pp. 221-226 (1997).
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Lee, Jennifer K., et al.; A pilot study of cerebrovascular reactivity autoregulation after pediatric cardiac arrest, Resuscitation 85, 2014, Elsevier Ireland Ltd., pp. 1387-1393.
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.
McGrath, S.P., et al.; "Pulse oximeter plethysmographic waveform changes in awake, spontaneously breathing, hypovolemic volunteers," Anesth. Analg. vol. 112 No. 2, pp. 368-374 (2010).
Montgomery, Dean, et al.; "Data cluestering methods for the determination of cerebral autoregulation functionality," Journal of Clinical Monitoring and Computing, vol. 30, No. 5, Sep. 16, 2015, pp. 661-668.
Morren, G., et al.; "Detection of autoregulation in the brain of premature infants using a novel subspace-based technique," 23rd Annual International Conference of IEEE Engineering in Medicine and Biology Society, Oct. 2001; pp. 1-4.
Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.
Neumann, R., et al.; "Fourier Artifact suppression Technology Provides Reliable $SpO_2$," Anesthesia & Analgesia 2002, 94: S105.
Obrig, Hellmuth, et al.; "Spontaneous low frequency oscillations of cerebral heodynamics and metabolism in human adults," NeuroImage 12, 623-639 (2000).
Odagiri, Y.; "Pulse Wave Measuring Device," *Micromechatronics*, vol. 42, No. 3, pp. 6-11 (published Sep. 1998) (Article in Japanese—contains English summary of article).
Ono, Masahiro, et al.; "Validation of a stand-alone near-infrared spectroscopy system for monitoring cerebral autoregulation during cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics—the macro- vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.
Shamir, M., et al.; "Pulse oximetry plethysmographic waveform during changes in blood volume," British Journal of Anaesthesia 82(2): 178-81 (1999).

(56) References Cited

OTHER PUBLICATIONS

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu, Dongmei, et al.; "Na*/H* Exchange inhibition delays the onset of hypovolemic circulatory shock in pigs," SHOCK, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal OF Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

International Search Report and Written Opinion from International Application No. PCT/US2016/031021, dated Aug. 5, 2016, 10 pp.

U.S. Appl. No. 15/666,167, filed Aug. 1, 2017, naming inventors Addison et al.

International Preliminary Report on Patentability from International Application No. PCT/US2016/031021, dated Nov. 23, 2017, 8 pp.

Communication Pursuant to Rules 161(1) and 162 EPC dated Dec. 15, 2017 from counterpart European Application No. 16724202.3, 3 pp.

Chuan et al., "Is cerebrovascular autoregulation associated with outcomes after major noncardiac surgery? A prospective observational pilot study," Acta Anaesthesiol Scand., Aug. 5, 2018, 10 pp.

Office Action from counterpart Canadian Application No. 2,982,855, dated Jul. 12, 2018, 6 pp.

Response to Canadian Office Action dated Jul. 12, 2018, from counterpart Canadian Patent Application No. 2,982,855, filed Jan. 10, 2019, 19 pp.

\* cited by examiner

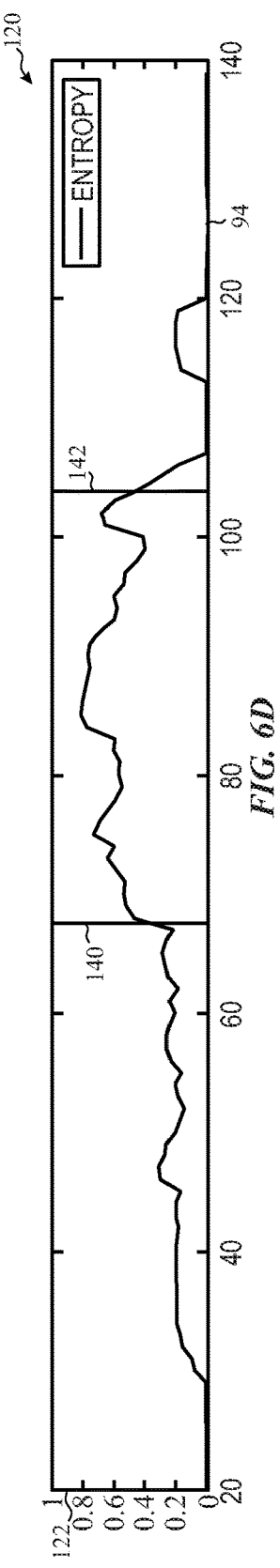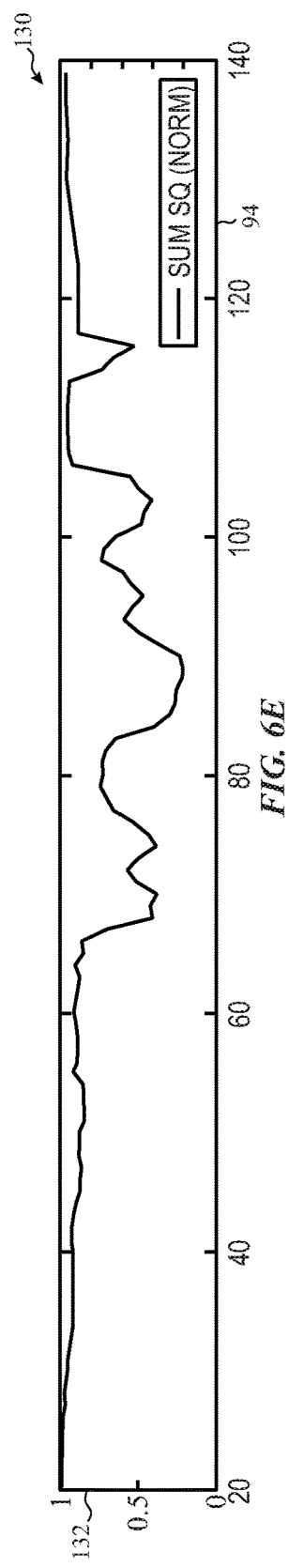

SYSTEM AND METHOD FOR IDENTIFYING AUTOREGULATION ZONES

CROSS-REFERENCE TO RELATED APPLICATION

This application claims priority to and the benefit of Provisional Application No. 62/158,659, entitled "SYSTEM AND METHOD FOR IDENTIFYING AUTOREGULATION ZONES," filed May 8, 2015, which is herein incorporated by reference in its entirety.

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. However, determining whether the patient's autoregulation is intact or impaired using typical existing systems may take several minutes, or even hours. In certain clinical settings, the extended time for determining whether the patient's autoregulation is intact or impaired may affect patient care and outcomes. Therefore, systems and methods for efficiently determining the patient's autoregulation status are provided herein.

BRIEF DESCRIPTION OF THE DRAWINGS

Advantages of the disclosed techniques may become apparent upon reading the following detailed description and upon reference to the drawings in which:

FIGS. 6A-6E are examples of graphs illustrating various clustering metrics that facilitate identification of an autoregulation zone.

DETAILED DESCRIPTION OF SPECIFIC EMBODIMENTS

Figure 1:
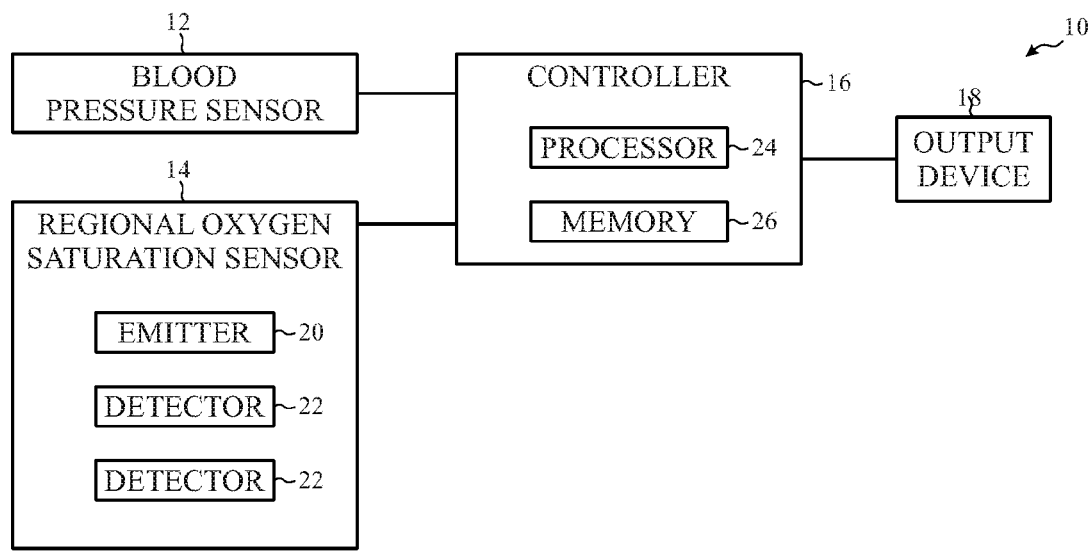
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) indicative of the patient's autoregulation status may be derived based at least in part on a linear correlation between the patient's blood pressure and oxygen saturation. In certain situations, it may be beneficial to identify autoregulation zones indicative of a patient's blood pressure dependent autoregulation status. A patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired.

Typical autoregulation monitoring techniques may identify these zones by determining an upper limit of autoregulation (ULA) value and/or a lower limit of autoregulation (LLA) that approximately define an upper and a lower blood pressure (e.g., mean arterial pressure or MAP) boundary, respectively, within which autoregulation is generally intact and functioning properly. Likewise, blood pressures approximately above the ULA and/or approximately below the LLA may be associated with impaired autoregulation function. In some cases, identifying the ULA, LLA, and/or autoregulation zones using such typical systems and methods may take several minutes, or even hours. For example, multiple blood pressure and oxygen saturation data points are typically obtained over an extended period of time (e.g., several minutes or hours), a COx curve is determined based on a linear correlation (e.g., regression line) between the blood pressure and oxygen saturation data points, and a point at which a step change from COx values of approximately 0 to COx values of approximately 1 occurs is utilized to identify the ULA or LLA. However, in certain clinical settings, the extended time for obtaining these data points and for determining the ULA, LLA, and autoregulation zones may affect patient care and outcomes. Accordingly, systems and methods for efficiently identifying blood pressures associated with the autoregulation zones, and thereby efficiently determining the patient's autoregulation status, are provided herein. Furthermore, in some embodiments, the system may be configured to provide information indicative of the autoregulation zones and/or autoregulation status to a user. Such systems and methods may in turn provide improved patient monitoring and patient care.

FIG. 1 illustrates an embodiment of a system 10 for monitoring autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., mean arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable identification of the autoregulation zone(s) and to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. A time processing unit (TPU) may provide timing control signals to light drive circuitry, which may be configured to control and/or to adjust the light emitted by the emitter 20. For example, the light drive circuitry may control and/or adjust when the emitter 20 is activated. The TPU and/or the light drive circuitry may be provided within the monitor 12 or the sensor 14.

One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status. While the depicted oxygen saturation sensor 14 is a regional saturation sensor, the sensor 14 may be a pulse oximeter configured to obtain the patient's oxygen saturation or may be any suitable sensor configured to provide a signal indicative of the patient's blood flow. For example, the sensor 14 may be configured to emit light at a single wavelength (e.g., an isobestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to determine the autoregulation zone(s) and/or to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

Figure 2:
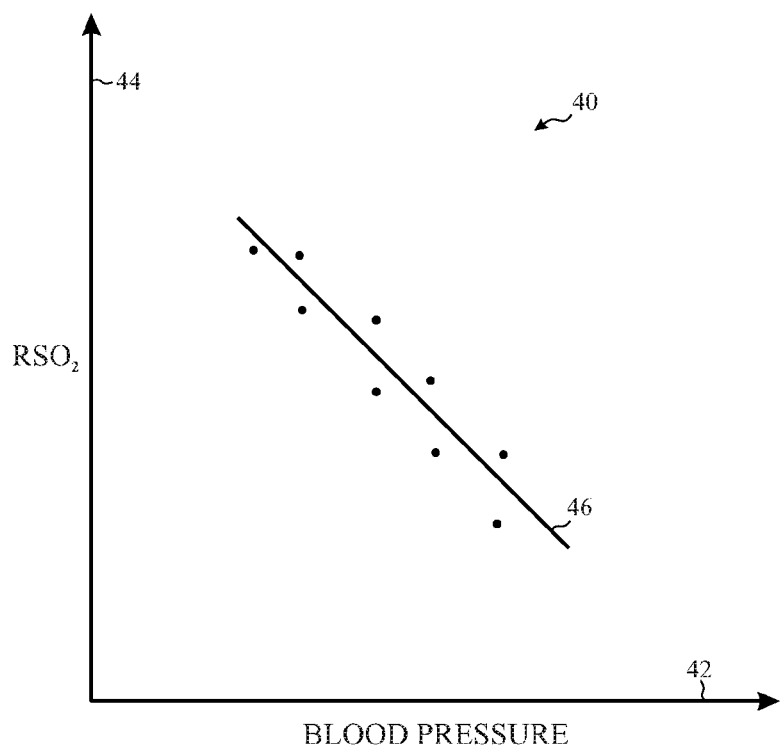
FIG. 2 is an example of a graph illustrating a linear correlation between oxygen saturation values and blood pressure values.

In some embodiments, the controller 16 may be configured to determine a cerebral oximetry index (COx) based on the blood pressure signal and the oxygen saturation signal. The COx is generally indicative of vascular reactivity, which is related to cerebral blood vessels' ability to control proper blood flow, via vasoconstriction (a narrowing of the blood vessel) and/or vasodilation (expansion of the blood vessel), for example. The controller 16 may derive a COx value by determining a linear correlation between blood pressure measurements and oxygen saturation measurements. With the foregoing in mind, FIG. 2 is an example of a graph 40 illustrating a linear correlation between blood pressure measurements 42 (e.g., arterial blood pressure measurements) and oxygen saturation measurements 44. The linear correlation may be based on a Pearson coefficient, for example. The Pearson coefficient may be defined as the covariance of the measured blood pressure (e.g., arterial blood pressure) and oxygen saturation divided by the product of their standard deviations. The result of the linear correlation may be a regression line 46 between the blood pressure measurements 42 and the oxygen saturation measurements 44, and the slope of the regression line 46 may be generally indicative of the patient's autoregulation status. In the illustrated example, the slope of the regression line 46 is negative and, thus, the COx value is between −1 and 0. However, when the regression line 46 has a positive slope, the COx value is between 0 and 1.

In some embodiments, the controller 16 may be configured to utilize the COx values to efficiently identify blood pressures associated with various autoregulation zones (e.g., a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired). Identifying blood pressures associated with the various autoregulation zones may, in turn, facilitate efficient determination of the patient's autoregulation status.

Figure 3A:
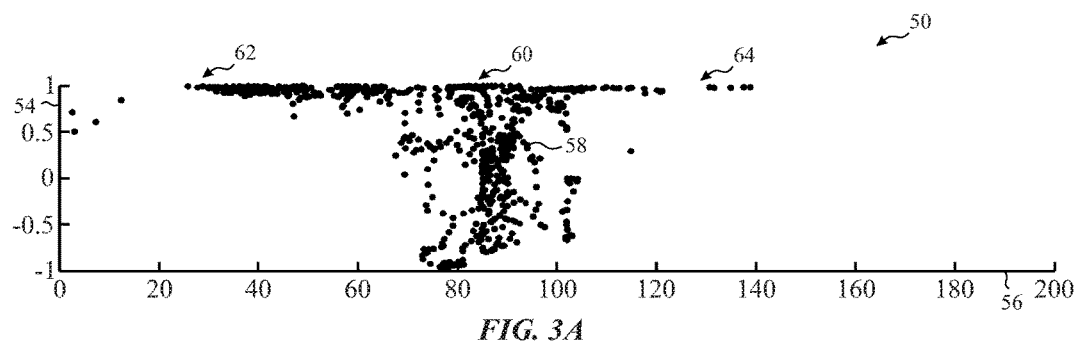
FIGS. 3A and 3B are examples of graphs illustrating cerebral oximetry index (COx) plotted against mean arterial pressure (MAP)
Figure 3B:
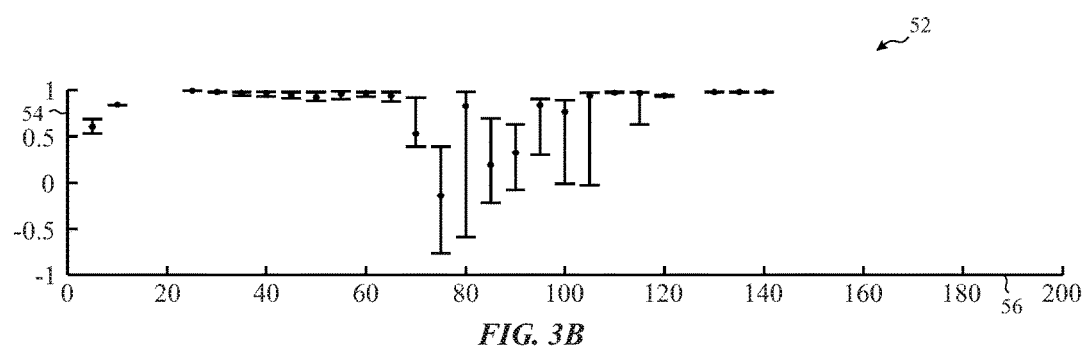

Graphs 50, 52 of FIGS. 3A and 3B illustrate the COx 54 plotted against blood pressure 56 (e.g., mean arterial pressure). In particular, the graph 50 of FIG. 3A illustrates individual data points 58 utilized to generate the graph 52 of FIG. 3B, in which the data points 58 are binned according to the blood pressure 56. As shown, the data points 58 are distributed (e.g., spread) across COx values 54 in a characteristic manner at the various blood pressures 56. In particular, the data points 58 may have a relatively greater spread across COx values 54 at intermediate blood pressures associated with an intact autoregulation zone 60. Additionally, the data points 58 may have a relatively lower spread across COx values 54 at lower blood pressures associated with a lower impaired autoregulation zone 62 and at higher blood pressures associated with a higher impaired autoregulation zone 64. Furthermore, the data points 58 may generally vary between −1 and +1 at the intermediate blood pressures associated with the intact autoregulation zone 60, and may cluster at approximately +1 at the lower blood pressures associated with the lower impaired autoregulation zone 62 and at the higher blood pressures associated with the higher impaired autoregulation zone 64. These distribution patterns and/or characteristics may be utilized to facilitate efficient determination of the blood pressures associated with various autoregulation zones. For example, any of a variety of clustering metrics may be utilized by the controller 16 to quantify the spread of the COx values 54 at each blood pressure 56 (e.g., at a single blood pressure or a range of blood pressures), and thereby, classify the blood pressure 56 as being within or being associated with one of the autoregulation zones, as discussed in detail below.

Returning to FIG. 1, in the illustrated embodiment, the controller 16 is an electronic controller that includes a processor 24 and a memory device 26. The controller 16 may also include one or more storage devices. The processor 24 may be used to execute software, such as software for carrying out any of the techniques disclosed herein, such as processing the blood pressure signals and/or oxygen saturation signals, determining a COx value, calculating a clustering measure, identifying autoregulation zones, causing display of information related to autoregulation zones and/or status on a display, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for processing the blood pressure signals and/or oxygen saturation signals, determining a COx value, calculating a clustering measure, identifying autoregulation zones, causing display of information related to autoregulation zones and/or status on a display, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the COx, thresholds, etc.), instructions (e.g., software or firmware for processing the blood pressure signals and/or oxygen saturation signals, determining a COx value, calculating a clustering measure, identifying autoregulation zones, causing display of information related to autoregulation zones and/or status on a display, and so forth), predetermined thresholds, and any other suitable data.

As shown, the system 10 includes the output device 18. In some embodiments, the controller 16 may be configured to provide signals indicative of the autoregulation zones and/or the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the current autoregulation zone and/or the patient's autoregulation status, the alarm signal, or the like) from the controller 16 and visually and/or audibly output information indicative of the patient's autoregulation status (e.g., the COx, the autoregulation zones, an alarm, a text message, or the like). For instance, the output device 18 may include a display configured to provide a visual representation of the patient's autoregulation status, autoregulation zones, and/or the COx as determined by the controller 16. Additionally or alternatively, the output device 18 may include an audio device configured to provide sounds in accordance with the patient's autoregulation status, the COx, and/or the autoregulation zones. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 4:
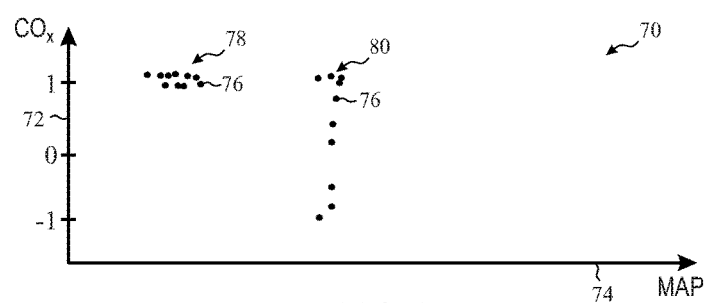
FIG. 4 is an example of a graph illustrating COx plotted against MAP to facilitate efficient identification of an autoregulation zone.

Presently disclosed systems and methods may enable efficient identification of blood pressures associated with the autoregulation zones. In FIG. 4, a graph 70 of COx 72 plotted against blood pressure 74 is shown. As data points 76 are calculated and plotted, the distribution patterns discussed above may become evident and may be quantified and/or analyzed to facilitate determination of which autoregulation zone the blood pressure (e.g., a single blood pressure or a range of blood pressures) falls within or is associated with. For example, a first group 78 of data points 76 at one blood pressure 74 (e.g., across a first range or within a first window of blood pressures 74) may generally cluster at a COx value of approximately +1, while a second group 80 of data points 76 at a second blood pressure 74 (e.g., across a second range or within a second window of blood pressures 74) may have a relatively greater spread across COx values. In some embodiments, each of the ranges or windows of blood pressures 74 may encompass approximately 1, 2, 3, 4, 5, 10, 15 mmHg or more. In some embodiments, the ranges or windows of blood pressures 74 may be of a fixed size (e.g., encompass a predetermined range of blood pressures), and in other embodiments, the ranges or windows may be dynamic and may encompass a variable range of blood pressures based on a number of data points obtained or collected (e.g., the range may be dynamically adjusted to encompass a predetermined number of data points 76, such as 3, 5, 8, 10, or more, for calculation of the spread across COx values within the range).

The controller 16 may be configured to quantify and/or analyze the distribution (e.g., spread across COx values) at each of these blood pressures 74. For example, as discussed in more detail below, the controller 16 may be configured to determine one or more of a range, a mean absolute deviation, an interquartile range, a variance, a sum of squares, an entropy measure, or any other suitable clustering metric to evaluate the distribution at the blood pressure 74. The clustering metrics noted herein are not intended to be limiting, and the controller 16 may be configured to evaluate the distribution via any of a variety of suitable techniques. Furthermore, one or more clustering metrics may be utilized in combination to evaluate the distribution.

Figure 5:
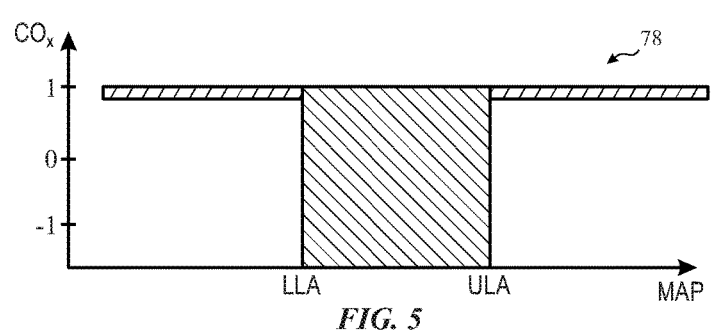
FIG. 5 is an example of a graph illustrating various autoregulation zones.

If the clustering metric indicates a relatively large distribution (e.g., above a predetermined threshold) at the blood pressure 74, then the controller 16 may determine that the blood pressure 74 is within the intact autoregulation zone. However, if the clustering metric indicates a relatively small distribution (e.g., below a predetermined threshold) at the blood pressure 74, then the controller 16 may determine that the blood pressure 74 is within one of the low impaired autoregulation zone or the high impaired autoregulation zone. Furthermore, the controller 16 may be configured to more precisely determine whether the blood pressure 74 is within the low or the high impaired autoregulation zone based at least in part on the clustering metric and an identified intact autoregulation zone (e.g., the low impaired autoregulation zone will include blood pressures below those of the intact autoregulation zone, while the high impaired autoregulation zone will include blood pressures above those of the intact autoregulation zone). By evaluating the distribution across COx values at various blood pressures, the controller 16 may efficiently determine which autoregulation zone the blood pressure falls within and/or may identify the blood pressures associated with each of the autoregulation zones. For example, in some embodiments, the controller 16 may be configured to determine which autoregulation zone the blood pressure falls within in less than 60, 30, 15, 10, 5, or 3 minutes. In some embodiments, the controller 16 may be configured to determine which autoregulation zone the blood pressure falls within in using less than 20, 15, 10, or 5 data points 76 at the blood pressure. In some embodiments, the controller 16 may be configured to gather and analyze a sufficient amount of data over time to estimate and/or to identify the LLA and/or the ULA and/or to generate a map 78 (e.g., picture, representation, or image) of the various autoregulation zones, an example of which is shown in FIG. 5.

In some embodiments, the controller 16 may be configured to determine a quality level (e.g., confidence metric or index value) related to the determined autoregulation zone. For example, as more data points 76 are added at the blood pressure 74 (e.g., within the window of blood pressures 74) and utilized in calculating the clustering metric at the blood pressure 74, the quality level may increase. In some embodiments, the controller 16 may be configured to provide an indication of the quality level to the output device 18 based on the number of data points 76 utilized to calculate the clustering metric at the blood pressure 74 (e.g., a visual or audible indication indicative of the quality level, such as a relatively high quality level if the number of data points 76 exceeds a predetermined threshold, such as 3, 5, 10, 15, or more data points, or a relatively low quality level if the number of data points 76 is below the predetermined threshold). In some embodiments, the controller 16 may be configured to calculate a range of COx values at the blood pressure 74 (e.g., within the window of blood pressures 74), and to divide the range of COx values by a number of data points 76 within the window of blood pressures 74 to determine a quality index. A large range and a low number of data points 76 results in a large quality index, which may be indicative of noise, and thus, a low quality level (e.g., confidence) in the clustering metric or autoregulation status determination. In some embodiments, the controller 16 may be configured to provide an indication of the quality level to the output device 18 (e.g., a visual or audible indication indicative of the quality level, such as a low quality level if the quality index exceeds a predetermined threshold, or a high quality level if the quality index is below the predetermined threshold).

Thus, in the disclosed embodiments, the controller 16 may be configured to efficiently determine which autoregulation zone the blood pressure falls within and/or identify the blood pressures associated with each of the autoregulation zones using a generally or relatively low number of data points (e.g., as compared to typical techniques). Furthermore, the controller 16 may be configured to identify blood pressures associated with each of the autoregulation zones without first determining the LLA or the ULA, which may take several minutes or hours in typical autoregulation monitoring methods. Additionally, in some embodiments, the controller 16 may be configured to estimate and/or identify the LLA and/or the ULA and/or to generate a map of the various autoregulation zones without relying on identification of a step change of COx values, as discussed above. The controller 16 may also be configured to determine a quality level related to the determined autoregulation zone and/or autoregulation status. Thus, the disclosed embodiments may enable efficient identification of the autoregulation status, and thus, may provide improved patient care and outcomes.

Figure 6A:

As noted above, any of a variety of clustering metrics may be utilized to quantify and/or evaluate the distribution and to identify the autoregulation zones. FIGS. 6A-6E are examples of graphs illustrating various measures (e.g., clustering metrics) that may facilitate identification of the autoregulation zones. In particular, FIG. 6A illustrates a graph 90 of COx 92 plotted against blood pressure 94 (e.g., mean arterial pressure). Similar to FIG. 3A, data points 96 of FIG. 6A are distributed (e.g., spread) across COx values 92 in a characteristic manner at various blood pressures 94. In particular, the data points 96 have a relatively greater spread across COx values 92 at intermediate blood pressures. Additionally, the data points 96 may have a relatively lower spread across COx values 92 at lower blood pressures and at higher blood pressures. Furthermore, the data points 96 generally vary between −1 and +1 at the intermediate blood pressures, and generally cluster at approximately +1 at the lower blood pressures and at the higher blood pressures.

Figure 6B:
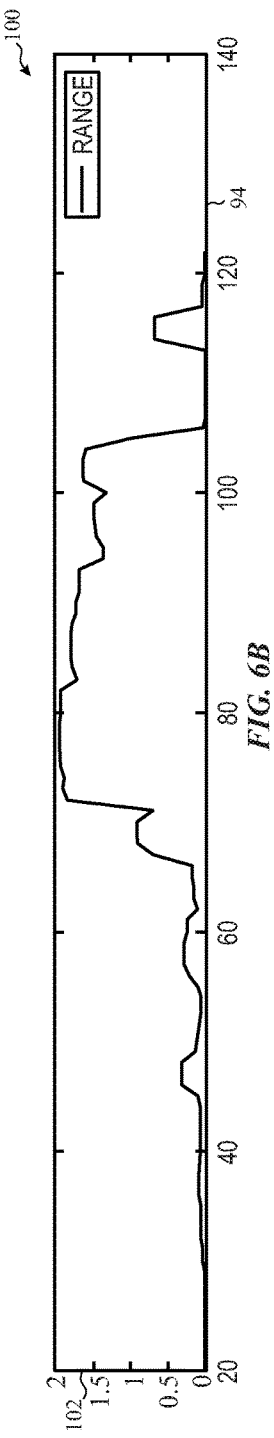

One or more clustering metrics may be utilized by the controller 16 to quantify and/or analyze the distribution of the data points 96, and thereby, determine which autoregulation zone each blood pressure value 94 falls within and/or identify the blood pressures associated with each of the autoregulation zones. FIG. 6B illustrates an example of a graph 100 of the range 102 of the COx values 92 at various blood pressures 94. In some embodiments, the controller 16 may be configured to compare the range 102 to one or more predetermined range thresholds (e.g., stored in the memory device 26) to determine whether the corresponding blood pressure is within the intact autoregulation zone or one of the impaired autoregulation zones. For example, the predetermined range threshold may be approximately equal to 1. In such cases, the controller 16 may be configured to determine that the blood pressure 94 is within an intact autoregulation zone 104 if the range 102 is greater than or equal to 1, and may determine that the blood pressure 94 is in one of the impaired autoregulation zones (e.g., the low impaired autoregulation zone 105 or the high impaired autoregulation zone 106) if the range 102 is less than 1. The predetermined range threshold of 1 is merely provided as an example, and it should be understood that the predetermined range threshold may be 0.5, 1, 1.5, or any other suitable threshold.

Figure 6C:
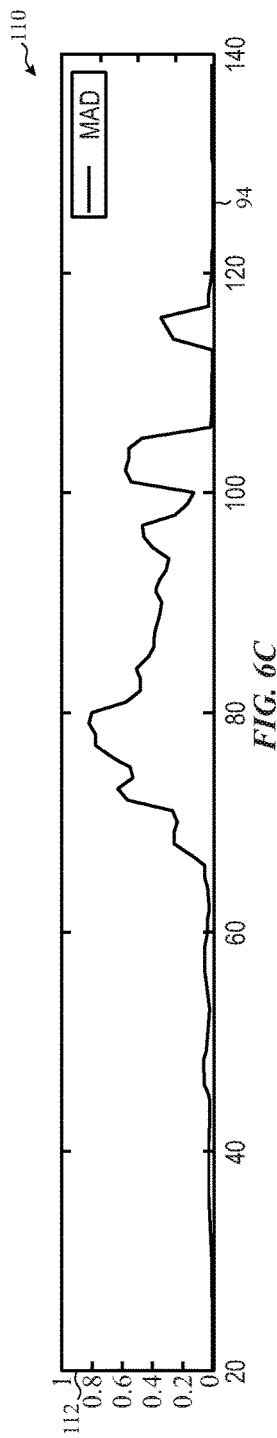

FIG. 6C illustrates an example of a graph 110 of a Mean Absolute Deviation (MAD) 112 of the COx values 92 at various blood pressures 94. In some embodiments, the controller 16 may be configured to compare the MAD 112 to one or more predetermined MAD threshold (e.g., stored in the memory device 26) to determine whether the corresponding blood pressure is within the intact autoregulation zone or one of the impaired autoregulation zones. For example, the predetermined MAD threshold may be approximately equal to 0.2, 0.4, 0.6, 0.8, or any other suitable threshold. In such cases, the controller 16 may be configured to determine that the blood pressure 94 is within the intact autoregulation zone 104 if the MAD 112 is greater than or equal to the predetermined MAD threshold, and may determine that the blood pressure 94 is in one of the impaired autoregulation zones (e.g., the low impaired autoregulation zone 105 or the high impaired autoregulation zone 106) if the MAD 112 is less than the predetermined MAD threshold.

FIG. 6D illustrates an example of a graph 120 of an entropy measure 122 of the COx values 92 at various blood pressures 94. Any suitable entropy measure may be utilized to quantify the clustering of the data points 96. For example, FIG. 6C is based on the following equation:

$$EN = 1/\Sigma P(i)^2 \qquad (1)$$

where P(i) is the probability that a data point will be in a given state or box. For example, if the data points 96 are clustered together (e.g., within a box), the entropy may approach 1 (e.g., may be less than 3, 2, 1). However, if the data points 96 are less clustered (e.g., divided into different boxes), the entropy may be greater than 1 (e.g., may be greater than 1, 2, 3, 4, or 5). In certain embodiments, the entropy measure may be calculated based on the following equation:

$$EN = \Sigma(1/P(i)) \qquad (2)$$

where P(i) is the probability that a data point, i, will be in a given state or box. In some embodiments, the entropy measure may be calculated based on Shannon Entropy or any other suitable data clustering measure.

In some embodiments, the controller 16 may be configured to compare the entropy measure 122 to one or more predetermined entropy thresholds (e.g., stored in the memory device 26) to determine whether the corresponding blood pressure 94 is within the intact autoregulation zone or one of the impaired autoregulation zones. For example, the predetermined entropy threshold may be approximately equal to 1, 2, 3, 4, or any other suitable threshold. In such cases, the controller 16 may be configured to determine that the blood pressure 94 is within the intact autoregulation zone 104 if the entropy measure 122 is greater than or equal to the predetermined entropy threshold, and may determine that the blood pressure 94 is in one of the impaired autoregulation zones (e.g., the low impaired autoregulation zone 105 or the high impaired autoregulation zone 106) if the entropy measure 122 is less than the predetermined entropy threshold.

FIG. 6E illustrates an example of a graph 130 of a sum of squares measure 132 of the COx values 92 at various blood pressures 94. In some embodiments, the controller 16 may be configured to compare the sum of squares measure 132 to one or more predetermined thresholds (e.g., stored in the memory device 26) to determine whether the corresponding blood pressure 94 is within the intact autoregulation zone or one of the impaired autoregulation zones. For example, the predetermined threshold may be approximately equal to 0.1, 0.2, 0.3, 0.4, 0.5, 0.6, 0.7, 0.8, 0.9 or any other suitable threshold. In such cases, the controller 16 may be configured to determine that the blood pressure 94 is within the intact autoregulation zone 104 if the sum of squares measure 132 is less than or equal to the predetermined threshold, and may determine that the blood pressure 94 is in one of the impaired autoregulation zones (e.g., the low impaired autoregulation zone 105 or the high impaired autoregulation zone 106) if the sum of squares measure 132 is greater than the predetermined threshold.

Furthermore, if one or more blood pressures 74 associated with the intact autoregulation zone have been previously identified (e.g., via any suitable clustering metric), the controller 16 may be configured to determine whether blood pressures 74 corresponding to relatively low spread (e.g., below respective thresholds) are within the low impaired autoregulation zone 105 or the high impaired autoregulation zone 106 based at least in part on the one or more blood pressures 74 associated with the intact autoregulation zone (e.g., the low impaired autoregulation zone will include blood pressures below those of the intact autoregulation zone, while the high impaired autoregulation zone will include blood pressures above those of the intact autoregulation zone). As noted above, in some embodiments, the controller 16 may be configured to estimate and/or identify the LLA and/or the ULA and/or to construct a map of the various autoregulation zones upon collection of sufficient data points 96 and calculation of corresponding clustering metrics. For example, with reference to FIG. 6D, the controller 16 may be configured to estimate an LLA 140 based on a point at which the entropy 122 crosses the predetermined range threshold and/or to estimate an ULA 142 based on a point at which the entropy 122 crosses the predetermined range threshold. Similarly, the controller 16 may be configured to estimate the LLA and/or the ULA based on points at which the range 102, the MAD 112, the sum of squares measure 132, or any other suitable clustering metric, cross respective predetermined thresholds. As noted above, any suitable predetermined thresholds may be utilized to classify blood pressures 74 as being within the intact autoregulation zone or one of the impaired autoregulation zones. In addition to or as an alternative to predetermined threshold values, the controller 16 may be configured to identify the various autoregulation zones based on step changes (e.g., increases or decreases of the clustering metric by more than a certain predetermined percentage, such as 1, 2, 3, 4, 5, 10, 25, 50, 75 percent or more) across blood pressures 74 (e.g., adjacent windows or ranges of blood pressures 74). Any of the suitable clustering metrics may be utilized together or in combination with one another. Additionally, the controller 16 may be configured to utilize one or more clustering metrics and/or the data points 96 in a classification algorithm, such as a decision tree algorithm, a k-nearest neighbors algorithm, and/or an artificial neural network to classify the blood pressure 76 as being within one of the autoregulation zones. Furthermore, the clustering metrics and techniques disclosed herein may be adapted for use with any of a variety of correlation-based measures indicative of the patient's autoregulation function, such as a hemoglobin volume index (HVx), a mean velocity index (Mx), and/or a pressure reactivity index (PRx). For example, a clustering metric may be applied to determine a spread of HVx, Mx, and/or PRx at various blood pressures, and the clustering metric may be utilized to classify the blood pressure 76 as being within one of the autoregulation zones.

Figure 7:
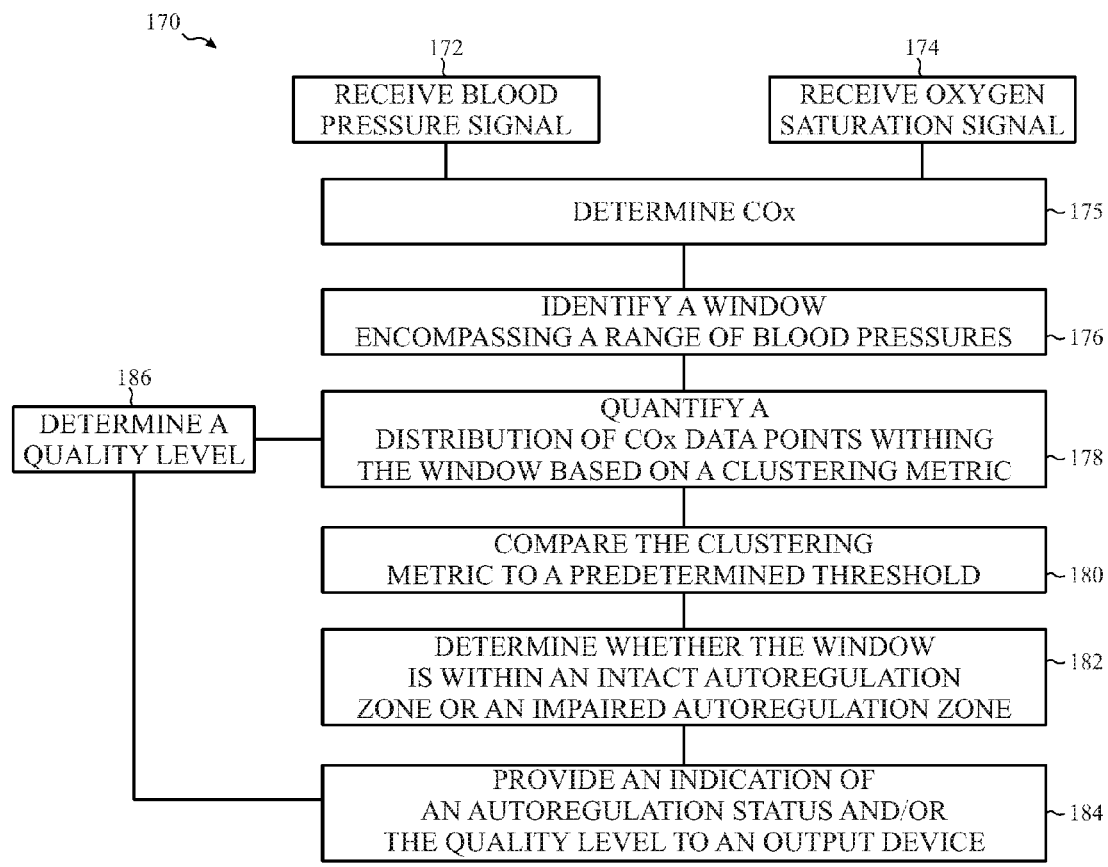
FIG. 7 is a process of an embodiment flow diagram of a method for determining an autoregulation status of a patient.

FIG. 7 is a process flow diagram of an embodiment of a method 170 of monitoring autoregulation, in accordance with an embodiment. The method 170 includes various steps represented by blocks. The method 170 may be performed as an automated procedure by a system, such as system 10. Although the flow chart illustrates the steps in a certain sequence, it should be understood that the steps may be performed in any suitable order, certain steps may be carried out simultaneously, and/or certain steps may be omitted, where appropriate. Further, certain steps or portions of the method 170 may be performed by separate devices. For example, a first portion of the method 170 may be performed by the controller 16, while a second portion of the method 170 may be performed by the sensor 14. In addition, insofar as steps of the method disclosed herein are applied to the received signals, it should be understood that the received signals may be raw signals or processed signals. That is, the method 170 may be applied to an output of the received signals.

In step 172, the controller 16 may receive the blood pressure signal (e.g., arterial blood pressure signal). In some embodiments, the controller 16 may receive the blood pressure signal from the blood pressure sensor 12, as set forth above. In step 174, the controller 16 may receive the oxygen saturation signal. In some embodiments, the controller 16 may receive the oxygen saturation signal from the oxygen saturation sensor 14, as set forth above. In step 175, the controller 16 may determine the COx based on the linear correlation between blood pressure measurements of the blood pressure signal and the oxygen saturation measurements of the oxygen saturation signal.

In step 176, the controller 16 may identify a window encompassing a range of blood pressures. For example, the window may encompass 1, 2, 3, 4, 5, 10, or more mmHg. As noted above, the window may be fixed or dynamically adjusted to encompass a predetermined number of COx data points. In step 178, the controller 16 may quantify a distribution of COx data points within the window based on any of a variety of clustering metrics, such as a range, a mean absolute deviation, an interquartile range, a variance, a sum of squares, an entropy measure, or any other suitable clustering metric, as discussed above with respect to FIGS. 6A-6E.

In step 180, the controller 16 may compare the clustering metric to a corresponding predetermined threshold (e.g., stored in the memory device 26). In step 182, the controller 16 may determine whether the blood pressures included within the window are within an intact autoregulation zone or an impaired autoregulation zone, and thus, may determine the autoregulation status of the patient. Accordingly, the controller 16 may determine blood pressures associated with each of the various autoregulation zones. As noted above, in some embodiments, the controller 16 may be configured to estimate and/or identify the ULA, LLA, and/or generate a map of the autoregulation zones upon collection of sufficient blood pressure and oxygen saturation data.

In step 184, the controller 16 may provide an output (e.g., to the output device 18) indicative of the autoregulation zones and/or the autoregulation status of the patient. As noted above, the output device 18 may be configured to provide a visual and/or audible indication of the patient's autoregulation status, autoregulation zones, and/or the COx as determined and/or provided by the controller 16.

In some embodiments, the controller 16 may determine a quality level associated with the clustering metric and the determination of the patient's autoregulation status at step 186. As discussed above, the controller 16 may be configured to determine a quality level (e.g., confidence metric) based at least in part on a number of data points utilized to calculate the clustering metric within the window. In some embodiments, the controller 16 may be configured to calculate a range of COx values within the window, and to divide the range of COx values by a number of data points within the window to determine a quality index. A large range and a low number of data points results in a large quality index, which may be indicative of noise, and thus, a low quality level (e.g., confidence) in the clustering metric or autoregulation status determination. In some embodiments, the controller 16 may be configured to provide an indication of the quality level to the output device 18, and the output device 18 may provide a visual or audible indication indicative of the quality level. In some embodiments, the controller 16 may be configured to provide the autoregulation status to the output device only when the quality level is acceptable (e.g., above a predetermined threshold).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation, the method comprising:
   receiving, by a processor and from one or more sensors, a first physiological signal indicative of a blood pressure of a patient and a second physiological signal indicative of blood oxygen saturation of the patient;
   determining, by the processor, a correlation-based measure indicative of the patient's autoregulation based at least in part on the first physiological signal and the second physiological signal;
   calculating, by the processor, a statistical data clustering metric indicative of two or more spreads of the correlation-based measure, each spread being within a respective window of blood pressures;
   determining, by the processor, whether each window of blood pressures is within an intact autoregulation zone or an impaired autoregulation zone based at least in part on the data clustering metric; and
   at least one of:
   presenting, via a display, information indicative of a patient's autoregulation status; or
   outputting, via an audio device, information indicative of the patient's autoregulation status,
   wherein the information indicative of the patient's autoregulation status is based on the determination of whether each window of blood pressure is within the intact autoregulation zone or the impaired autoregulation zone.

2. The method of claim 1, wherein the data clustering metric comprises an entropy metric.

3. The method of claim 1, wherein the data clustering metric comprises a Mean Absolute Derivation.

4. The method of claim 1, wherein the data clustering metric comprises a sum of squares.

5. The method of claim 1, wherein the data clustering metric comprises at least one of a range, an interquartile range, or a variance.

6. The method of claim 1, wherein determining whether each window of blood pressures is within the intact autoregulation zone or the impaired autoregulation zone comprises comparing the data clustering metric to a predetermined threshold.

7. The method of claim 6, comprising, for at least one window of blood pressures, determining that blood pressures within the at least one window of blood pressures are within the intact autoregulation zone if the data clustering metric is greater than the predetermined threshold.

8. The method of claim 1, comprising, for at least one window of blood pressures, determining a quality level related to the determination of whether the at least one window of blood pressures is within the intact autoregulation zone or the impaired autoregulation zone based at least in part on a number of data points of the correlation-based measure utilized to calculate the data clustering metric for the at least one window of blood pressures.

9. The method of claim 1, comprising, for at least one window of blood pressures, determining which autoregulation zone encompasses the at least one window of blood pressures in less than approximately 15 minutes.

10. The method of claim 1, wherein the correlation-based measure includes at least one of a cerebral oximetry index, a hemoglobin volume index, a mean velocity index, or a pressure reactivity index.

11. The method of claim 1, comprising:
   determining the autoregulation status of the patient based on the determination of whether each window of blood pressures is within the intact autoregulation zone or the impaired autoregulation zone.

12. A non-transitory computer-readable medium comprising computer executable code stored thereon, the code comprising instructions that, when executed by a processor, cause the processor to:
   receive a blood pressure signal and an oxygen saturation signal;
   determine a correlation-based measure indicative of the patient's autoregulation based at least in part on the blood pressure signal and the oxygen saturation signal;
   calculate a statistical data clustering metric indicative of two or more spreads of the correlation-based measure, each spread being within a respective window of blood pressures;
   determine whether each window of blood pressures is within an intact autoregulation zone or an impaired autoregulation zone of a patient based at least in part on the data clustering metric; and
   at least one of:
   present, via a display, information indicative of a patient's autoregulation status; or output, via an audio device, information indicative of the patient's autoregulation status, wherein the information indicative of the patient's autoregulation status is based on the determination of whether each window of blood pressure is within the intact autoregulation zone or the impaired autoregulation zone.

13. The non-transitory computer-readable medium of claim 12, wherein the data clustering metric comprises at least one of an entropy metric, a range metric, a Mean Absolute Derivation metric, a sum of squares, an interquartile range, or a variance.

14. A system for monitoring autoregulation, the system comprising:

an oxygen saturation sensor configured to generate an oxygen saturation signal indicative of blood oxygen saturation of a patient; and a controller comprising a processor configured to:

receive a blood pressure signal and the oxygen saturation signal;

determine a correlation-based measure indicative of the patient's autoregulation based at least in part on the blood pressure signal and the oxygen saturation signal;

calculate a statistical data clustering metric indicative of two or more spreads of the correlation-based measure, each spread being within a respective window of blood pressures;

determine whether each window is associated with an intact autoregulation zone or an impaired autoregulation zone based at least in part on the data clustering metric; and at least one of:

present, via a display, information indicative of a patient's autoregulation status; or output, via an audio device, information indicative of the patient's autoregulation status, wherein the information indicative of the patient's autoregulation status is based on the identification of whether each window of blood pressure is within the intact autoregulation zone or the impaired autoregulation zone.

15. The system of claim 14, wherein the data clustering metric comprises at least one of an entropy metric, a range metric, a Mean Absolute Derivation metric, a sum of squares, an interquartile range, or a variance.

16. The system of claim 14, wherein the processor is configured to:

determine the autoregulation status of the patient based on the determination of whether each window of blood pressures is associated with the intact autoregulation zone or the impaired autoregulation zone.

17. The system of claim 14, wherein the processor is configured to determine whether each window of blood pressures is within the intact autoregulation zone or the impaired autoregulation zone by at least comparing the data clustering metric to a predetermined threshold.

18. The system of claim 17, wherein the processor is configured to determine, for at least one window of blood pressures, that blood pressures within the at least one window of blood pressures are within the intact autoregulation zone if the data clustering metric is greater than the predetermined threshold.

19. The system of claim 14, wherein the processor is configured to determine, for at least one window of blood pressures, a quality level related to the determination of whether the at least one window of blood pressures is within the intact autoregulation zone or the impaired autoregulation zone based at least in part on a number of data points of the correlation-based measure utilized to calculate the data clustering metric for the at least one window of blood pressures.

20. The system of claim 14, wherein the processor is configured to determine, for at least one window of blood pressures, which autoregulation zone encompasses the at least one window of blood pressures in less than approximately 15 minutes.

21. The system of claim 14, wherein the correlation-based measure includes at least one of a cerebral oximetry index, a hemoglobin volume index, a mean velocity index, or a pressure reactivity index.

* * * * *